United States Patent [19]

Oglevee et al.

[11] Patent Number: 4,570,379
[45] Date of Patent: Feb. 18, 1986

[54] LILY PROCESSES

[75] Inventors: James R. Oglevee; James F. Tammen, both of Connellsville; Wendy O. O'Donovan, Scottdale, all of Pa.

[73] Assignee: Oglevee Associates, Inc., Connellsville, Pa.

[21] Appl. No.: 559,035

[22] Filed: Dec. 7, 1983

[51] Int. Cl.$^4$ .......................... A01C 1/00; A01H 3/02
[52] U.S. Cl. ..................................... 47/58; 47/DIG. 3
[58] Field of Search ............................. 47/58, DIG. 3

[56] References Cited

U.S. PATENT DOCUMENTS

| | | | |
|---|---|---|---|
| 1,789,068 | 1/1931 | Colle et al. | 47/58 |
| 1,998,238 | 4/1935 | Howeth | 47/58 |
| 4,338,745 | 7/1982 | Misawa et al. | 47/58 |

OTHER PUBLICATIONS

Emsweller, S. L., "Lilies", *The Maryland Gardener*, vol. 4, No. 6, Jun. 1950, pp. 2 and 3.
Smith, S. H. et al., "Meristem-Tip Culture from Virus-Infected Plant Material and Cultural Implications", (taken from) *Plant Cell and Tissue Culture Principles and Applications*, W. R. Sharpe et al. (Eds.), Columbus, Ohio State University Press, pp. 453-460.
Hartmann, H. T. et al., "15: Propagation by Specialized Stems and Roots";16: Principles of Tissue Culture for Micropropagation, *Plant Propagation Principles and Practices*, (4th Ed.), Prentice-Hall, (1983), pp. 500, 501, 550-553.

*Primary Examiner*—James R. Feyrer
*Attorney, Agent, or Firm*—Webb, Burden, Robinson & Webb

[57] ABSTRACT

An improved method of growing an Easter lily or other species of the genus Lilium is disclosed. A bulb scale from a substantially pathogen-free lily plant is propagated in a growing medium to form a bulblet which is thereafter grown in plant form rather than bulb form. The bulblet is planted and the young plant is grown under conditions of short days to prevent flowering and encourage foliage and root formation. After the initial short-day growing period of approximately thirty-four weeks, a three week period of long-day conditions initiates flowering. Subsequently, a three month period of natural lighting effects the final growth and finishing of the desired lily plant.

17 Claims, 5 Drawing Figures

U.S. Patent    Feb. 18, 1986    4,570,379
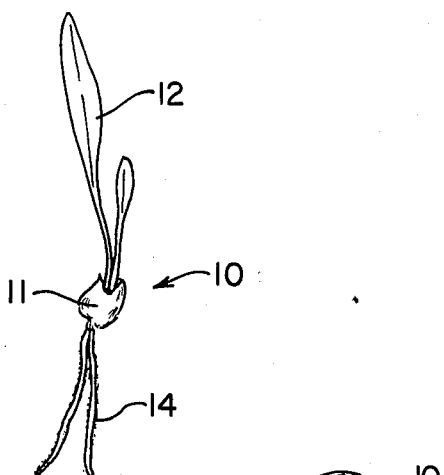
FIG. 1
FIG. 2
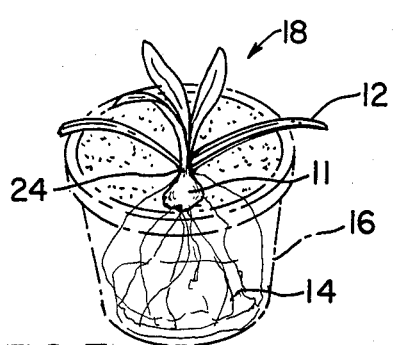
FIG. 3
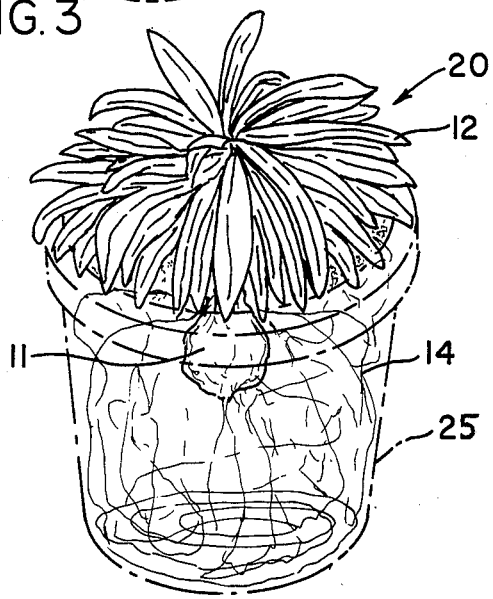
FIG. 4
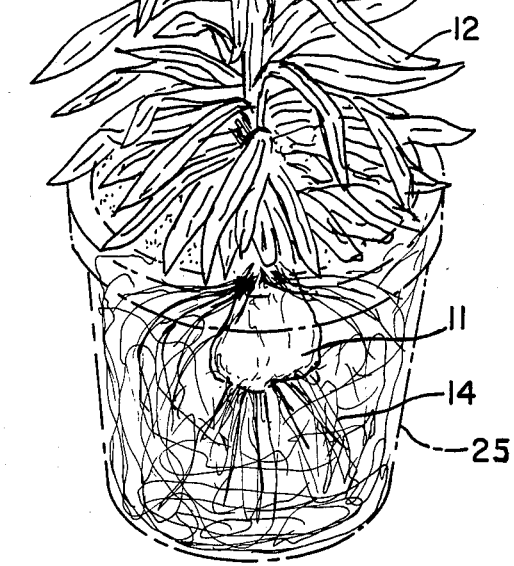
FIG. 5

LILY PROCESSES

BACKGROUND OF THE INVENTION

Our invention relates to the production of lilies, and more particularly, to the production of lilies, such as the Easter lily in plant form rather than in bulb form.

DESCRIPTION OF THE PRIOR ART

Lilies (the genus Lilium) have been used in religious ceremonies for over 2,000 years. The Easter lily (Lilium longiflorum) is the best known and the most valuable species of the genus Lilium, *Easter Lilies,* H. F. Wilkins, *Introduction to Floriculture,* Academic Press, Inc. 1980. The Lilium longiflorum was introduced in England about 1819 and almost immediately became one of the most popular plants in commercial floriculture when it gained general acceptance as the Easter plant. The Easter lily is a native of Japan and Japan was exporting Lilium longiflorum bulbs to Europe and the United States as early as 1876.

Easter lilies are grown from bulbs which function as the storage organ for starches and other nutrients and which include a growing plant (apical meristem) from which the stem emerges. The bulb goes through at least a two-year growth cycle and normally a three-year growth cycle before it is ready to be forced into an Easter plant or cut flowers for Easter. During this three-year period, all of the energy is going into the bulb to increase the bulb size and store up the necessary starches and other nutrients so as to permit proper growth of the plant in preparation for Easter. The bulbs have a memory which captures the climate and growing conditions of each year of growth. Therefore, no two sequential crops of lilies will behave alike and this variation makes it very difficult for the lily forcer to have all the plants or flowers ready on time. In addition, since the bulb gone through a three-year cycle, there is an increased chance of virus, root, vascular wilt or other diseases incited by plant pathogens.

A typical bulb growing cycle is as follows. In the first year the bulb grower starts with the scales of a mother bulb and sows the scales in a row. The scales grow into bulblets of one to three inches in circumference with the bulblets having a small root system and shoots. In the fall of the year, the bulblets are dug and thereafter sorted, cleaned and graded. During this process many of the roots and shoots are removed. In the spring of the second year the bulblets are planted in a field and grown so as to increase in size. The bulblet is now referred to as a bulb or a yearling. The average size of the bulb at the end of the second year is three inches to seven inches in circumference with some of the larger ones being ready to sell. Again in the fall the bulbs are dug up and cleaned and graded and during this process many of the roots and tops are again removed. In the third year, the bulbs are planted in the fields in the spring and they continue to enlarge to about seven to ten inches in circumference at which time they are dug up and ready to go to market.

In October of the third year, Easter lily bulbs are shipped to a greenhouse operator who forces the bulb for Easter. The objective is to have the plant fully grown and flowering at the desired time so as to provide cut flowers for the flower market or pot plants for the pot plant market.

To flower quickly, the bulb is precooled by putting it in a refrigerator below say 40° F. for about six weeks. Natural cooling may also be used by placing the bulbs in the ground. The advantage of natural cooling is that it increases the number of flowers per stem. It is also possible to plant the bulbs in greenhouses and force by temperature and day length to get blooms. If it is desired to delay flowering, the bulbs are stored at a high temperature, for example 60° F. for extended periods. Thereafter, the bulbs are precooled and forced.

For the pot plant market, the same procedure is used as for the cut flower market except the bulbs are placed in pots. More critical controls must be implemented since foliage and size are now critical, as well as number of flowers per plant. Effective cooling is to condition the bulb to give a quick, uniform emergence. For many years it was believed that lilies were photoneutral, which means they were not affected by differences in day length. More recently it was found that Easter lilies are responsive to a photoperiod and that lilies won't flower in short days but will flower in long days. Short-day plants require a dark period exceeding some critical length in order to flower, and long-day plants are inhibited from flowering when the dark period exceeds some critical length.

DESCRIPTION OF THE DRAWINGS

FIG. 1 is a schematic of a young Easter lily plantlet resulting from leaf propagation;

FIG. 2 is a schematic of a young Easter lily plantlet grown in a three inch container (shown in phantom) and planted immediately after leaf propagation;

FIG. 3 is a schematic of a well-established Easter lily plant in a three inch container (shown in phantom) and ready for transplanting;

FIG. 4 is a schematic of a well-established Easter lily plant in a six inch container (shown in phantom) with forty to fifty leaves in rosette form on a short stem; and FIG. 5 is a schematic of a mature, flowering Easter lily.

SUMMARY OF THE INVENTION

It is an object of our invention to eliminate the bulb as the storage organ and forcing unit for the lily. The energy is absorbed into leaves and roots of plants and not into a bulb. It is also an object of our invention to reduce and eliminate disease in lilies. It is further an object of our invention to eliminate the three-year period needed to grow bulbs and to provide lilies for the flower market or pot plant market within a one-year period or shorter. It is further an object of our invention to provide a plant which can be flowered for Easter and which can be grown in pot plant form to a size of eighteen to twenty-four inches in height with four to six flowers and eighty to ninety leaves.

Our method of growing a species of the genus Lilium comprises propagating from a substantially pathogen-free lily plant and in a growing media to form a bulblet which is thereafter grown in plant form rather than bulb form. The bulb is immediately planted in a greenhouse under aseptic conditions and grown under conditions of short days to prevent flowering and encourage foliage and root formation to form young plants. The young plants are then grown under similar conditions of short days to prevent flowering and encourage foliage and root formation to form plants having a large number of leaves rosette in form and an extensive root system. Thereafter the plant is grown under long days to initiate flowering and thereafter it is grown under natural lighting to the desired finished plant.

The complete growing cycle takes place within a one-year period or less and fungal, bacterial and virus pathogens are detected and eliminated by culture indexing and/or culture virus indexing the propagating units. In a preferred form of growing Easter lilies, the bulblet is formed through leaf propagation in ten weeks or less, the bulblet is placed in a small pot and grown into a young plant in about ten weeks and thereafter the young plant is transplanted into a larger pot and is grown for an additional fourteen weeks to form a plant having on the order of forty to fifty leaves rosette in form and an extensive root system. Thereafter the plant is grown under long-day conditions for about two weeks to initiate flowering and thereafter the plant is grown under natural lighting for about three months to form a plant of about eighteen to twenty-four inches in height including the pot and with about four to six flowers and about eighty to ninety leaves.

DESCRIPTION OF THE PREFERRED EMBODIMENTS

The preferred embodiment is directed to the growing of Easter lilies, although the same process can be used with the other lily species of the genus Lilium.

The process is initiated utilizing bulb scales from selected mother plants. To assure against disease in the final product, it is necessary to culture index and later to virus index to detect and eliminate root disease pathogens, vascular wilt pathogens and viruses. Culture indexing is used to determine if a vascular pathogen is present in a given bulb scale. A clean, selected bulb scale is removed from the bulb and surface sterilized. Under aseptic conditions, a section of the bulb scale is removed and placed into test tubes containing an agar growing medium rich in nutrients and sugar to which growth-regulating substances and vitamins have been added. If the scale section tested contains any of the fungal or bacterial pathogens, the pathogens grow from the section and onto the surface of the agar medium.

After a two-week incubation period at room temperature, the tubes are observed for growth of fungi and/or bacteria. If bacteria have been introduced into the tube, slimy bacterial growth will be noted. If fungi have been introduced in the tube, fuzzy, cobweb-like growth will be noted. The tube and scale section showing such growth are then discarded without need to identify the bacteria or fungi. Any scale sections testing negative are incubated under certain temperature and light conditions and within twelve weeks or less new bulblets form on the surface. The resulting bulblets are then transferred to a pasteurized soilless growing medium under strict sanitation as individual growing units in an isolated block termed "nucleus block" in the greenhouse. Rather than increase these units by starting with a scale from a lily mother plant in the nucleus block, we start with a leaf cutting. Leaf cuttings are then taken from the nucleus block to build a number of clean bulblets and the resultant plants are termed the increase block. By an identical procedure leaf cuttings from the increase block then serve to provide bulblets for production and scale of plants.

In order to culture virus index, cuttings are initially culture indexed as set forth above. Thereafter, a bioassay or other suitable method is used to virus index.

The lily plants must first be culture indexed using the procedure described above, thereafter with tissue culture and the scale pieces the resultant bulblets in the tubes must then be meristem-tip cultured. This is done by taking very small growing tips (of a millimeter or less) and placing them on fresh growing medium. These meristem tips are then grown in vitro until they are three to four centimeters in height and 0.3-0.5 centimeters in diameter. They are then planted into sterile soil and placed in the greenhouse. The plants are then ready to be virus indexed. Virus indexing is a visual method of testing for a virus.

There are various methods of indexing for viruses, one of which is bioassay which utilizes live plants. Plants that are sensitive to the viruses being tested are first grown. Specifically, plant portions of the lily to be tested are ground in a buffer solution. The resultant slurry is then gently rubbed onto the leaves of the indexing plants. After a period of time, which varies from weeks to months, the plants are observed for viral symptoms.

Another method of indexing for plant viruses utilizes electron microscopy. For this indexing method, a preparation of lily plant sap is observed under the electron microscope for the presence of virus particles.

Another method of virus indexing is ELISA which stands for Enzyme-Linked-Imuno-Sorbant Assay. This type of virus indexing assay can be done in the laboratory and is relatively quick, and extremely sensitive. However, ELISA is very specific and can not be used for all plant viruses. There are also other methods of virus indexing that are being perfected at this time and which could be used for virus indexing lilies in the future.

Depending upon the specific virus being tested, any or all of the above listed methods may be used for indexing lilies. Those plants indexing negative, that is showing no viruses present, will be considered a CVI (culture virus indexed) lily and continue through the system.

Leaves from culture virus indexed lily plants are stuck in a steamtreated propagation bench in a greenhouse and grown into a bulblet of approximately 0.6 to 1.2 inches in circumference. Generally, up to four bulblets may grow from a single leaf. The bulblets are removed from the propagation bench and are thereafter graded and cleaned. Each bulblet 10, includes a small number of hearty leaflets 12 and roots 14, FIG. 1. The time from leaf propagation to removing the bulblets is on the order of ten weeks or less.

Thereafter, the bulblets 10 are immediately planted in a greenhouse in small pots 16 three inches in diameter under aseptic conditions which preclude introduction of plant pathogens or their insect vectors, FIG. 2. The bulblets are grown under standard growing techniques, except that short days are employed. While a short day is normally considered anything less than twelve hours, we have found that a short day consisting of eight hours is optimum. The short day prevents flowering and helps establish the foliage and procedure a green plant. At this stage our goals are not to grow a bulb but to grow a plant 18, with our objective being increasingly abundant roots 14 and leaves 12. The plant 18 grown is rosette in form on a very short stem 24. The growth from the bulblet into the young plant takes on the order of ten weeks or less, FIG. 3.

The young plant is then transplanted into a six inch pot 25 and again grown for fourteen weeks or less under short-day conditions. The size of the plant dictates the size of the pot, with the smaller pot presenting a more acceptable growing environment for the small plant and the six inch pot presenting a more acceptable growing environment for the large root system and plant. Standard growing conditions are employed which consist of growing the plant in a soilless growing medium with constant fertilizer at luxury levels of nutrients and moisture. The daytime temperature is on the order of 70° F. and the nighttime temperature is on the order of 60° F. The change in pot size accommodates the increasing plant size and presents a more compatible growing environment.

At the end of this thirty-four week cycle, (10+10+14) the plant 20 now has on the order of forty to fifty leaves 12 and a substantial number of roots 14, yet the height of the plant 20 is still only about three inches or less, FIG. 4. The plant is rosette in form. The roots are primarily of the basal type, although some stem roots appear. The bulb has perhaps doubled in size but is still on the order of only two inches in circumference.

The next step is to continue growing the plant in its six inch pot but now under long-day conditions which consist of fourteen to sixteen hours of light. Lighting is at about fifteen foot candles and this growing stage takes on the order of two weeks. During the two-week period, flowering is initiated so that the plant now will bolt and grow to flower.

After the flowering has been initiated under long-day conditions, the artificial light is removed and the plant is grown under natural lighting up until Easter, which growing period is on the order of three months. At the end of three months, the plant 22 is now eighteen to twenty-four inches in height including the pot and there are four to six flowers 26 along with eighty to ninety leaves 12 and a plurality of roots 14, FIG. 5. The bulb is still on the order of only two to two and one half inches in circumference. By transplanting into the six inch pot on or before Sept. 15–Oct. 1, the flowering and bolting is initiated by the middle of January and the three months of growth under natural lighting results in a pot plant ready for the Easter season.

The resultant plant has taken a year or less to grow and there is substantial uniformity from plant to plant since there is no longer a memory period associated with the three-year bulb development. In addition, disease has been minimized and a healthy, full-grown plant is available at the appropriate time.

We claim:

1. A method of growing a species of the genus Lilium comprising:
   A. propagating from a substantially pathogen-free lily plant and in a growing media to form a bulblet;
   B. growing the bulblet under conditions to prevent flowering and encourage foliage and root formation to form a young plant;
   C. growing the young plant under conditions to prevent flowering and encourage foliage and root formation to form a plant having a large number of leaves rosette in form and an extensive root system;
   D. growing said plant under conditions to initiate flowering and bolting; and
   E. thereafter growing said plant to the desired plant condition.

2. The method of claim 1 including removing the bulblet from the growing media and planting the bulb immediately in a greenhouse under aseptic conditions.

3. The method of claim 2 including grading and sorting the bulblet prior to planting in a greenhouse.

4. The method of claim 2 including planting the bulblet in small pots in a greenhouse.

5. The method of claim 1 including selecting the species Lilium longiflorum from the genus Lilium.

6. The method of claim 1 including forming the bulblet to a size of at least 0.6 to 1.2 inches in circumference in ten weeks.

7. The method of claim 1 including growing the bulblet under short-day conditions.

8. The method of claim 6 including transplanting the young plant into a large pot prior to step E of claim 1.

9. The method of claim 1 including growing the young plant under short-day conditions.

10. The method of claim 1 including growing the plant under long-day conditions to cause flower initiation and bolting.

11. The method of claim 1 including culture indexing to select the pathogen-free lily plant.

12. The method of claim 1 including culture virus indexing to select the pathogen-free lily plant.

13. A method of growing Lilium longiflorum comprising:
   A. propagating from a substantially pathogen-free lily plant; by removing a portion of the plant
   B. growing the portion in a growing media for about ten weeks to form bulblets on the order of 0.6 to 1.2 inches in circumference;
   C. digging, grading and cleaning the bulblets;
   D. immediately planting the bulblet in a small pot in a greenhouse under aseptic conditions;
   E. growing the bulblet under short-day conditions to prevent flowering and establish foliage and roots for about ten weeks to form a young plant;
   F. transplanting the young plant to a larger pot and further growing the young plant under short-day conditions for about fourteen weeks to form a plant having on the order of forty to fify leaves rosette in form and an extensive root system;
   G. growing the plant under long-day conditions for about two weeks to initiate flowers; and
   H. growing the plant under natural lighting for up to about three months to a plant of about eighteen to twenty-four inches including the pot with about four to six flowers and about eighty to ninety leaves.

14. The method of claim 13 wherein the short days are on the order of eight hours and the long days are on the order of fourteen to sixteen hours.

15. The method of claim 13 including culture indexing to select the pathogen-free lily plant.

16. The method of claim 13 including culture virus indexing to select the pathogen-free lily plant.

17. The method of claim 13 including growing the bulblet, the young plant and the plant in soilless growing medium with a constant fertilizer at luxury levels of nutrients and moisture with approximately 70° F. day temperatures and approximately 60° F. night temperatures.

* * * * *